United States Patent
Martin et al.

(10) Patent No.: US 8,163,537 B2
(45) Date of Patent: Apr. 24, 2012

(54) NESTED PERMEABLE SUPPORT DEVICE AND METHOD FOR USING THE NESTED PERMEABLE SUPPORT DEVICE

(75) Inventors: Gregory R. Martin, Acton, ME (US); Allison J. Tanner, Portsmouth, NH (US)

(73) Assignee: Corning Incorporated, Corning, NY (US)

( * ) Notice: Subject to any disclaimer, the term of this patent is extended or adjusted under 35 U.S.C. 154(b) by 332 days.

(21) Appl. No.: 12/420,114

(22) Filed: Apr. 8, 2009

(65) Prior Publication Data
US 2010/0190197 A1 Jul. 29, 2010

Related U.S. Application Data

(60) Provisional application No. 61/147,562, filed on Jan. 27, 2009.

(51) Int. Cl.
*C12M 1/34* (2006.01)
*C12M 3/00* (2006.01)
*C12M 1/12* (2006.01)

(52) U.S. Cl. .............. 435/288.4; 435/284.1; 435/288.2; 435/288.3; 435/288.5; 435/305.1; 435/305.2; 435/297.1; 435/297.5

(58) Field of Classification Search .............. 435/284.1, 435/288.2, 288.3, 288.4, 288.5, 305.1, 305.2, 435/297.1, 297.5
See application file for complete search history.

(56) References Cited

U.S. PATENT DOCUMENTS

| | | | |
|---|---|---|---|
| 5,208,161 A * | 5/1993 | Saunders et al. | 422/534 |
| 5,409,829 A | 4/1995 | Mussi et al. | 435/240.241 |
| 5,443,950 A | 8/1995 | Naughton et al. | 435/1 |
| 5,470,743 A | 11/1995 | Mussi et al. | 435/297.1 |
| 5,583,037 A | 12/1996 | Mussi et al. | 435/240.241 |
| 5,665,596 A | 9/1997 | Mussi | 435/373 |
| 2004/0087005 A1* | 5/2004 | Henderson et al. | 435/283.1 |
| 2004/0091397 A1 | 5/2004 | Picard | 422/90 |
| 2004/0101955 A1* | 5/2004 | Whitley | 435/304.1 |
| 2006/0110822 A1 | 5/2006 | Robbins et al. | 435/289.1 |
| 2007/0020689 A1 | 1/2007 | Caracci et al. | 435/7.1 |
| 2007/0122904 A1 | 5/2007 | Nordon | 435/325 |
| 2007/0264682 A1 | 11/2007 | Besne | 435/29 |
| 2007/0298451 A1* | 12/2007 | Ribault et al. | 435/30 |

FOREIGN PATENT DOCUMENTS
WO    WO 2007/144355    12/2007

OTHER PUBLICATIONS

C.H. Ahn et al., "High Hepatic.Function Was Maintained on Electrospun Nanofibrous Scaffold", *Key Engineering Materials*, 2007, vols. 342-343, pp. 197-200.

M. Bokhari et al., "Culture of HepG2 liver cells on three dimensional polystyrene scaffolds enhances cell structure and function during toxicological challenge", *Journal of Anatomy.*, 2007, p. 1-10.

(Continued)

*Primary Examiner* — Nathan Bowers
(74) *Attorney, Agent, or Firm* — Susan S. Wilks

(57) ABSTRACT

A nested permeable support device is described herein that can be used to perform various experiments to test new therapeutic compounds (new chemical entities). In one application, the nested permeable support device is used to perform a first pass assay to determine the bioavailability of a new chemical entity following absorption through the digestive tract and metabolism by the liver.

11 Claims, 7 Drawing Sheets

OTHER PUBLICATIONS

S.H. Choi et al., "Feasibility of a simple double-layered coculture system incorporating metabolic processes of the intestine and liver tissue : application to the analysis of benzo[a]pyrene toxicity", *Toxicology in Vitro*, 2004, vol. 18, pp. 393-402.

Y. Du et al., "3D hepatocyte monolayer on hybrid RGD/galactose substratum", *Biomaterials*, 2006, vol. 27, pp. 5669-5680.

G.S. Grover et al., "Development of In Vitro Methods to Predict Induction of CYP1A2 and CYP3A4 in Humans", *Assay and Drug Development Technologies*, 2007, vol. 5, No. 6, pp. 793-804.

K. Isoda et al., "Maintenance of Hepatocyte Functions by Coculture with Bone Marrow Stromal Cells", *Journal of Bioscience and Bioengineering*, 2004, vol. 97, No. 5, pp. 343-346.

S.R. Khetani et al., "Microscale culture of human liver cells for drug development", Nature Biotechnology, Nov. 18, 2007, pp. 1-7.

Y.Y. Lau et al., "Evaluation of a Novel In Vitro CACO-2 Hepatocyte Hybrid System for Predicting In Vivo Oral Bioavailability", *Drug Metabolism and Disposition*, 2004, vol. 32, No. 9, pp. 937-942.

P.V. Moghe et al., "Culture matrix configuration and composition in the maintenance of hepatocyte polarity and function", *Biomaterials*, 1996, vol. 17, No. 3, pp. 373-385.

S. Ng et al., "Optimization of 3-D hepatocyte culture by controlling the physical and chemical properties of the extra-cellular matrices", *Biomaterials*, 2005, vol. 26, pp. 3153-3163.

U.S. Department of Health and Human Services, et al., "Guidance for Industry—Drug Interaction Studies—Study Design, Data Analysis, and Implications for Dosing and Labeling", Clinical Pharmacology, Sep. 2006.

"Corning HTS Transwell®—96 Permeable Supports: How to Optimize Performance", Corning Incorporated, 2005.

\* cited by examiner

NESTED PERMEABLE SUPPORT DEVICE AND METHOD FOR USING THE NESTED PERMEABLE SUPPORT DEVICE

CLAIMING BENEFIT OF PRIOR FILED U.S. APPLICATION

This application claims the benefit of U.S. Provisional Application Ser. No. 61/147,562 entitled "Nested Permeable Supports" filed on Jan. 27, 2009 the contents of which are hereby incorporated by reference herein.

TECHNICAL FIELD

The present invention relates in general to a nested permeable support device and method for using the nested permeable support device to perform various experiments to test new therapeutic compounds (new chemical entities). In one application, the nested permeable support device is used to perform a first pass assay to determine the bioavailability of a new chemical entity following absorption through the digestive tract and metabolism by the liver.

BACKGROUND

The following abbreviations are herewith defined, at least some of which are referred to within the following description of the state-of-the-art and the present invention. The reference to the "present invention" or "invention" used herein relates to exemplary embodiments and not necessarily to every embodiment that is encompassed by the appended claims.
ADME-Tox Absorption, Distribution, Metabolism, Excretion and Toxicity
ASGPR Asialoglycoprotein Receptor
ECM Extracellular Matrices
US FDA United States Food Drug Administration
HTS High-Throughput Screening
LC Liquid Chromatography
MS Mass Spectroscopy
NCE New Chemical Entity
SBS Society of Biomolecular Screening
TEER Trans Epithelial Electrical Resistance The following references are cited below in the description of the state of-the-art, where their contents are hereby incorporated by reference herein.
1. Yau Yi Lau et al. "Evaluation of a Novel In Vitro Caco-2 Hepatocyte Hybrid System for Predicting In Vivo Oral Bioavailability" Drug Metabolism and Disposition, Vol. 32, No. 9, pp. 937-942, 2004.
2. "Transwell® Permeable Supports: Including Snapwell™ and Netwell™ Inserts—Instructions for Use" Corning Inc., September 2007.
3. Sue Hyung Choi et al. "Feasibility of Simple Double-Layered Coculture System Incorporating Metabolic Processes of the Intestine and Liver Tissue: Application to the Analysis of Benzo[a]pyrene Toxicity", Toxicology in Vitro, vol. 18, pages 393-402, 2004.
4. U.S. Department of Health and Human Services et al. "Guidance for Industry: Drug Interaction Studies-Study, Design, Data Analysis, and Implications for Dosing and Labeling", Clinical Pharmacology, September 2006.

In the search for new therapeutic drugs, pharmaceutical companies utilize many different methods to determine whether a compound or molecule known as a NCE has a desired biological activity. These methods often entail examining the ADME-Tox of the NCE, as well as determining the NCE's level of effectiveness for the targeted therapeutic indication including pharmacokinetic parameters. One type of assessment examines the "first pass effect". This assessment involves experimental determination of the bioavailabilty of the NCE following its absorption through the digestive tract and then its metabolism by the liver. Commonly, the assessment of the "first pass effect" requires two separate in vitro assays to be conducted, and the data combined, to determine the intestinal permeability and the hepatic metabolism. If desired, additional studies may be conducted to determine target selectivity, efficacy and dosage (reference no. 1).

A well-known method used today to examine the intestinal absorption of a NCE is known as the Caco 2 cell-based assay which is typically conducted on permeable supports such as the ones sold under the brand name of Transwell™ and manufactured by Corning Inc. (reference no. 2). The design of the Transwell™ permeable support facilitates the development of Caco 2 cell polarization to create more in vivo-like test conditions. Researchers from the Schering-Plough Research Institute have expanded the utility of the Caco 2 cell-based assay by adding hepatocytes in the nutrient medium to a Transwell™ receiver plate which receives the Transwell™ permeable support. In this way, the researchers were able to more accurately predict the oral bioavailability of NCE's. However, the hepatic cell viability under these conditions during a 3 hour incubation period was only 50-70%, limiting the potential of this method (reference no. 1). Another group of researchers from the University of Tokyo co-cultured Caco-2 cells on the Transwell™ permeable support with monolayers of Hep G2 cells growing on the inner surface of the Transwell™ receiver plate. While useful for some assays, the Hep G2 cells did not maintain the functions that are representative of in vivo hepatocytes (reference no. 3).

The current US FDA Guidance regarding drug interaction studies like the first pass assay recommends the use of in vitro assays with fresh or cryopreserved human hepatocytes due to species specific responses (reference no. 4). However, it is well known that primary hepatocytes loose differentiated function rapidly in standard cell culture conditions on tissue culture treated polystyrene. The loss of normal differentiated hepatocyte function decreases the in vivo-like conditions and hence also decreases the relevance of experimental data in ADME-Tox and pharmacokinetic in vitro assays. Thus, any enhancement of test equipment and conditions to provide a more in vivo-like situation for the cells in culture would greatly improve the relevance of the information which is gained by these types of experiments.

SUMMARY

In one aspect, the present invention provides a nested permeable support device including: (a) a first well having at least a portion of a bottom formed by a first permeable support; (b) a second well having at least a portion of a bottom formed by a second permeable support, where the second well and the second permeable support are located below the first well and the first permeable support; and (c) a third well having a bottom which is located below the second well and the second permeable support.

In another aspect, the present invention provides a method for performing an experiment to test a new chemical entity. The method including the steps of: (a) providing a nested permeable support device which has a first well having at least a portion of a bottom formed by a first permeable support, where the first permeable support has at least one first cell layer formed thereon, a second well having at least a portion of a bottom formed by a second permeable support, where the second permeable support has at least one second cell layer formed thereon, where the second well and the second permeable support are located below the first well and the first permeable support; and a third well having a bottom which is located below the second well and the second permeable support; (b) adding media to the second well and the third well; (c) adding media and the new chemical entity to the first well; and (d) interrogating the media in at least one of the second well and the third well to determine if at least a portion of the new chemical entity passed through the first permeable support and the second permeable support.

In yet another aspect, the present invention provides a nested permeable support device including: (a) a first insert including a first well and a first permeable support, where the first permeable support forms at least a portion of a bottom of the first well; (b) a second insert including a second well and a second permeable support, where the second permeable support forms at least a portion of a bottom of the second well, where the first insert is configured to be placed at least partially within the second insert so that the second well and the second permeable support are located below the first well and the first permeable support; and (c) a reservoir including a third well having a bottom formed by a receiver plate, the reservoir is configured to receive the second insert and the first insert.

In still yet another aspect, the present invention provides a nested permeable support device configured like a microplate including: (a) a first insert plate having a plurality of first inserts where each first insert includes a first well and a first permeable support, where the first permeable support forms at least a portion of a bottom of the first well; (b) a second insert plate having a plurality of second inserts where each second insert includes a second well and a second permeable support, where the second permeable support forms at least a portion of a bottom of the second well, where the first insert plate is configured to be stacked on the second insert plate such that the first inserts are at least partially located within the second inserts; and (c) a reservoir plate having a plurality of reservoirs, where the second insert plate is configured to be stacked on the reservoir plate such that the second inserts are at least partially located within the reservoirs.

In yet another aspect, the present invention provides a nested permeable support device including: (a) a first sheet having an opening used to form a first well, where the first sheet has a top on which there is attached a permeable film and a bottom on which there is attached a first permeable support, where the permeable film has at least one opening formed therein to provide access to the first well; (b) a second sheet having an opening used to form a second well, where the second sheet has a top on which there is attached the first permeable support and a bottom on which there is attached a second permeable support, where each of the permeable film, the first sheet and the first permeable support has at least one opening formed therein to provide access to the second well; and (c) a third sheet having an opening used to form a third well, where the third sheet has a top on which there is attached the second permeable support and a bottom on which there is attached a receiver plate, wherein each of the permeable film, the first sheet, the first permeable support, the second sheet and the second permeable support has at least one opening formed therein to provide access the third well.

Additional aspects of the invention will be set forth, in part, in the detailed description, figures and any claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE DRAWINGS

A more complete understanding of the present invention may be had by reference to the following detailed description when taken in conjunction with the accompanying drawings wherein.

DETAILED DESCRIPTION

A nested permeable support device is described below where the nested permeable support device can be used to perform a wide variety of experiments to test NCEs. The nested permeable support device includes: (a) a first well having at least a portion of a bottom formed by a first permeable support; (b) a second well having at least a portion of a bottom formed by a second permeable support, where the second well and the second permeable support are located below the first well and the first permeable support; and (c) a third well having a bottom which is located below the second well and the second permeable support. Two exemplary embodiments of the nested permeable support device and how they can be used to perform a first pass assay are described in detail below with respect to FIGS. 1-4.

Figure 1A:
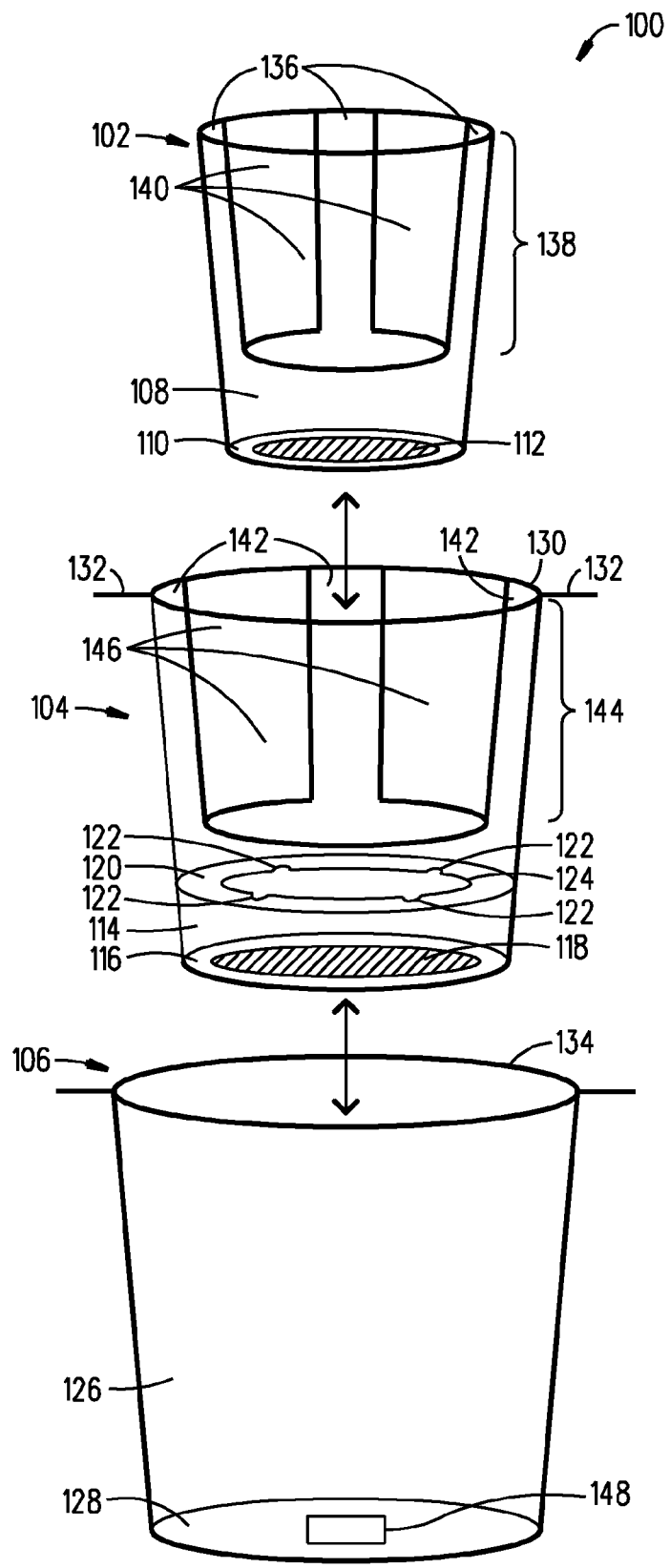
FIGS. 1A-1C show different views of an exemplary nested permeable support device configured in accordance with an embodiment of the present invention.
Figure 1B:
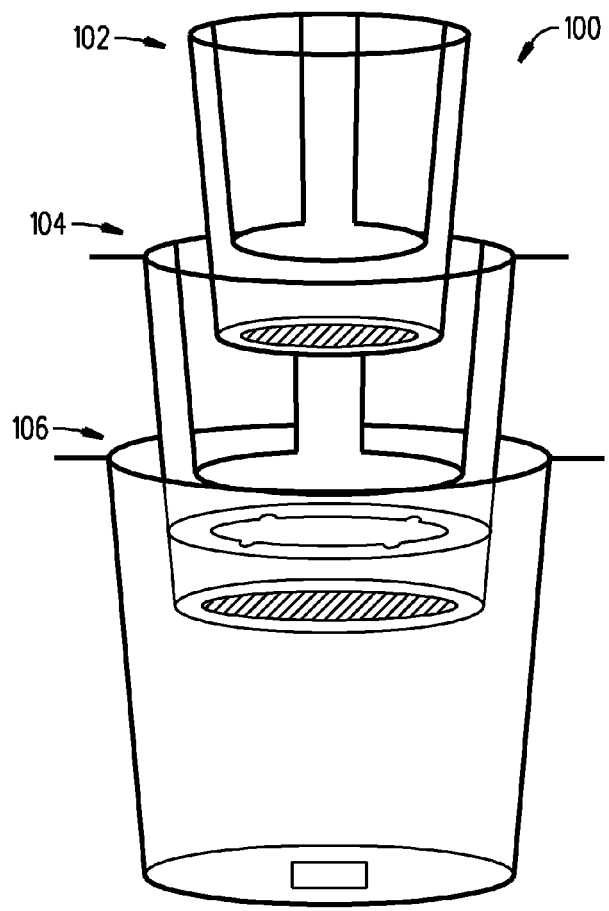
Figure 1C:
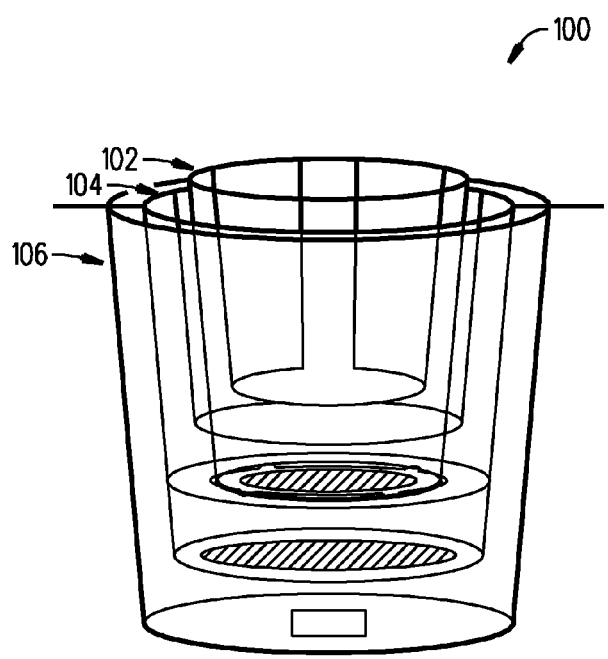

Referring to FIGS. 1A-1C, there are shown several different diagrams of an exemplary nested permeable support device 100 in accordance with an embodiment of the present invention. The nested permeable support device 100 includes a first insert 102 which is sized to be placed within a second insert 104 which itself is sized to be placed within a reservoir 106. In FIG. 1A, there is shown a perspective view of the nested permeable support device 100 where the first insert 102 is separated from the second insert 104, and the second insert 104 is separated from the reservoir 106. In FIG. 1B, there is shown a perspective view of the nested permeable support device 100 where the first insert 102 is partially located within the second insert 104, and the second insert 104 is partially located within the reservoir 106. In FIG. 1C, there is shown a perspective view of the nested permeable support device 100 where the first insert 102 is supported within the second insert 104, and the second insert 104 is supported within the reservoir 106. In this last configuration, the nested permeable support device 100 is ready to be used to perform an experiment to test a NCE.

As shown, the first insert 102 includes a first well 108 (fluid compartment 108) which has a bottom 110 that is formed at least in part by a first permeable support 112. The second insert 104 includes a second well 114 (fluid compartment 114) which has a bottom 116 that is formed at least in part by a second permeable support 118. The second insert 104 further includes an inner ledge 120 extending around an inner perimeter thereof and located above the second well 114, where the inner ledge 120 is sized to support the bottom 110 of the first insert 102. If desired, the inner ledge 120 can have one or more indentations 122 (four shown) formed on an outer edge 124 thereof where the indentation(s) 122 permit air to escape from the second well 114 when the first insert 102 is placed within the second insert 104. The reservoir 106 is configured and sized to receive the second insert 104. The reservoir 106 has the third well 126 (fluid compartment 126) with a bottom 128 (receiver plate 128) which is located below the second permeable support 118. To enable the reservoir 106 to support the second insert 104 and by default the first insert 102, the second insert 104 has an upper edge 130 with an extension 132 protruding outward which can engage and be supported by an upper edge 134 of the reservoir 106. If desired, the first insert 102 can have an extension protruding from an upper edge which would enable the first insert 102 to be supported by the upper edge 130 of the second insert 104. In this case, the first insert 102 would not need to incorporate the inner ledge 120.

In this example, the first insert 102 has three supports 136 formed in an upper wall 138 which creates three openings 140 in the upper wall 138. The three supports 136 are sized to maintain the shape of the first well 108 (fluid compartment 108). Typically, the body of the first insert 102 would be a molded or thermoformed polystyrene but could also be made from different polymers including, for example, polyethylene, polypropylene and cyclic olefin. Alternatively, the first insert 102 could be made from any suitable material such as metal or glass. The first permeable support 112 could be a track-etched membrane, a woven porous material, or a non-woven porous material. Alternatively, the first permeable support 112 may have electro-spun fibers, or some other matrix material or gel structure that enhances differentiated function for specific cell types. If desired, the first permeable support 112 could be treated by corona, radio frequency or microwave plasma to enhance cell attachment.

The second insert 104 in this example has three supports 142 formed in an upper wall 144 which creates three openings 146 in the upper wall 144. The three supports 142 are sized to maintain the shape of the second well 114 (fluid compartment 114). Typically, the body of the second insert 104 would be a molded or thermoformed polystyrene but could also be made from different polymers including, for example, polyethylene, polypropylene and cyclic olefin. Alternatively, the second insert 104 could be made from any suitable material such as metal or glass. The second permeable support 118 could be a track-etched membrane, a woven porous material, or a non-woven porous material. Alternatively, the second permeable support 118 may have electro-spun fibers, or some other matrix material or gel structure that enhances differentiated function for specific cell types. If desired, the second permeable support 118 could be treated by corona, radio frequency or microwave plasma to enhance cell attachment. The first and second permeable supports 112 and 118 may have the same treatment or coating or different treatments or coatings.

The reservoir 106 would typically be a molded or thermoformed polystyrene but could also be made from different polymers including, for example, polyethylene, polypropylene and cyclic olefins. Alternatively, the reservoir 106 could be made from any suitable material such as metal or glass. As will be discussed below, the reservoir's third well 126 contains fluid that would be typically interrogated by LC/MS.

However, the reservoir's bottom 128 (receiver plate 128) could be derivatized to support differentiated function for specific cell types. In addition, the receiver plate 128 could be made with an optically clear, possibly gas-permeable material to facilitate high-content screening. Yet another option for the receiver plate 128 would be to feature a biosensor 148 (e.g., grating-based planar waveguide sensor, grating-based surface plasmon resonance sensor, prism-based surface plasmon resonance sensor) that enables, for example, the detection of a specific biochemical ligand or dynamic mass redistribution occurring in cells growing on the biosensor 148 by using an interrogation system. For instance, the interrogation system could be configured like the ones described in co-assigned U.S. Patent Publication No. 2007 0020689 A1 and co-assigned U.S. Patent Publication No. 2004 0091397 A1 (the contents of which are incorporated by reference herein).

Figure 2A:
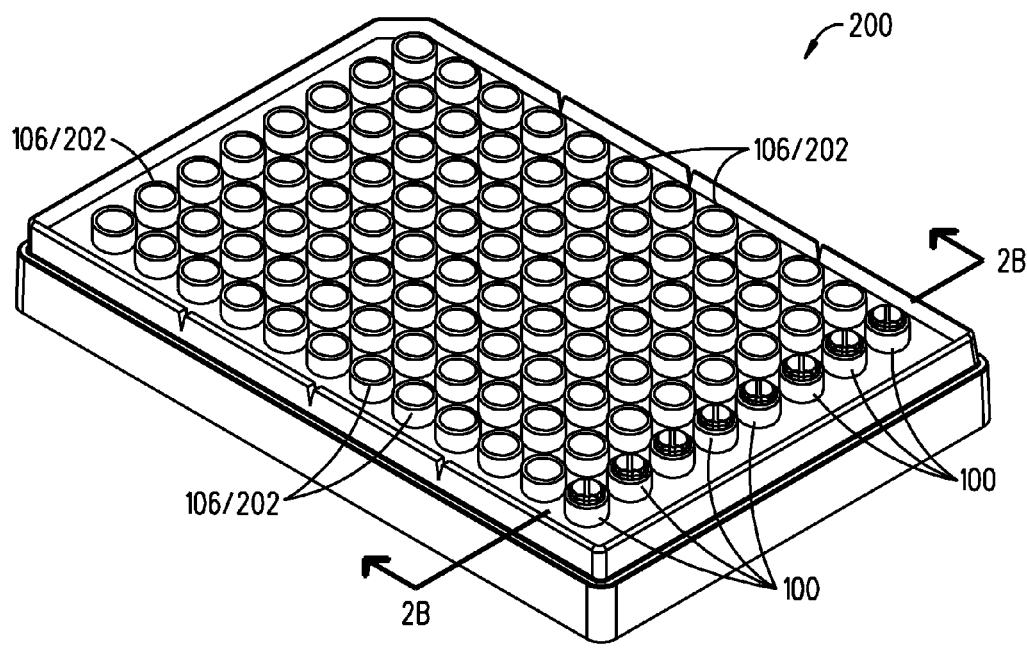
FIGS. 2A-2B respectively illustrate a perspective view and a cross-sectional side view of an exemplary microplate incorporating several of the nested permeable support devices shown in FIGS. 1A-1C.
Figure 2B:
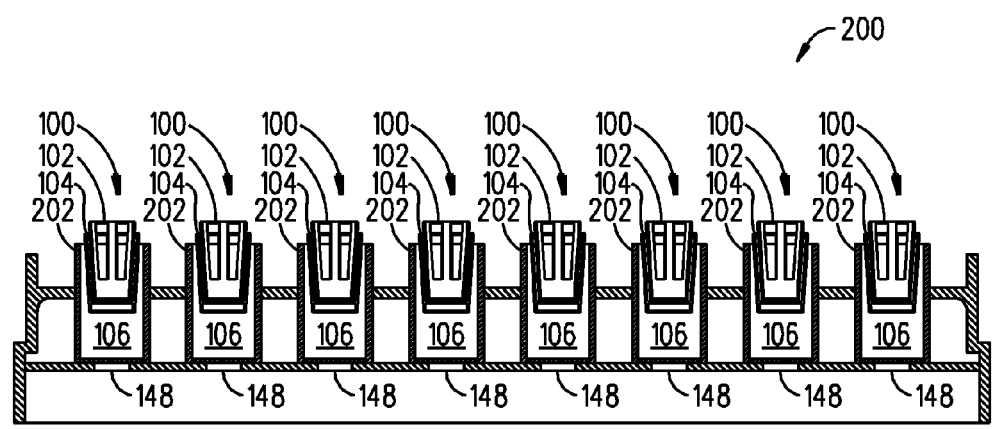

A person could use a single nested permeable support device 100 to perform an experiment to test a NCE. Alternatively, the person could use multiple nested permeable support devices 100 in a multiwell format to perform multiple experiments at the same time. Referring to FIGS. 2A-2B, there are respectively illustrated a perspective view and a cross-sectional side view of an exemplary microplate 200 incorporating multiple nested permeable support devices 100 (only eight shown). The microplate 200 includes an array of wells 202 each of which can function as the reservoir 106 to receive the first and second inserts 102 and 104. In this example, the bottom of each well 202 (reservoir 106) is shown incorporating the optional biosensor 148. The wells 202 are generally arranged in a matrix of mutually perpendicular rows and columns. For example, the microplate 200 can include a matrix of wells 202 having dimensions of 4×6 (24 wells), 8×12 (96 wells), 16×24 (384 wells), 32×48 (1536 wells) etc. . . . The microplate 200 shown includes an array of ninety-six wells 202 and can have SBS dimensions which would be well-suited to permit robotic handling.

Figure 2C:
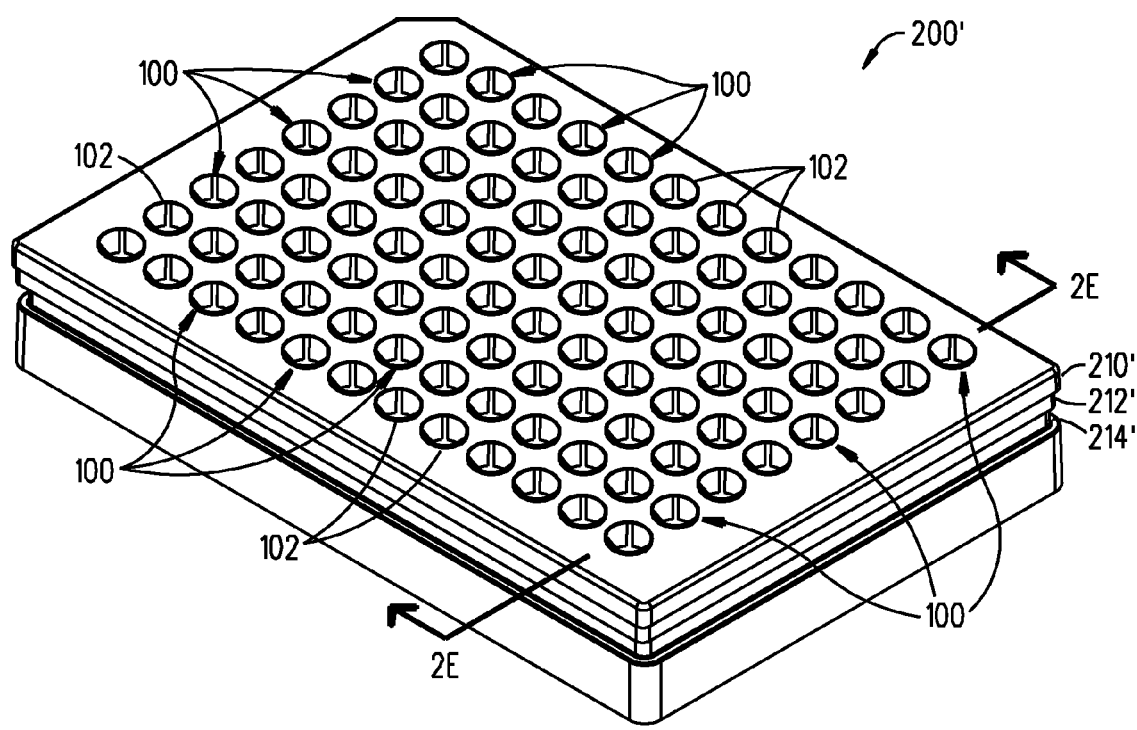
FIGS. 2C-2E show different views of several nested permeable support devices shown in FIGS. 1A-1C coupled to one another to form of an exemplary microplate.
Figure 2D:
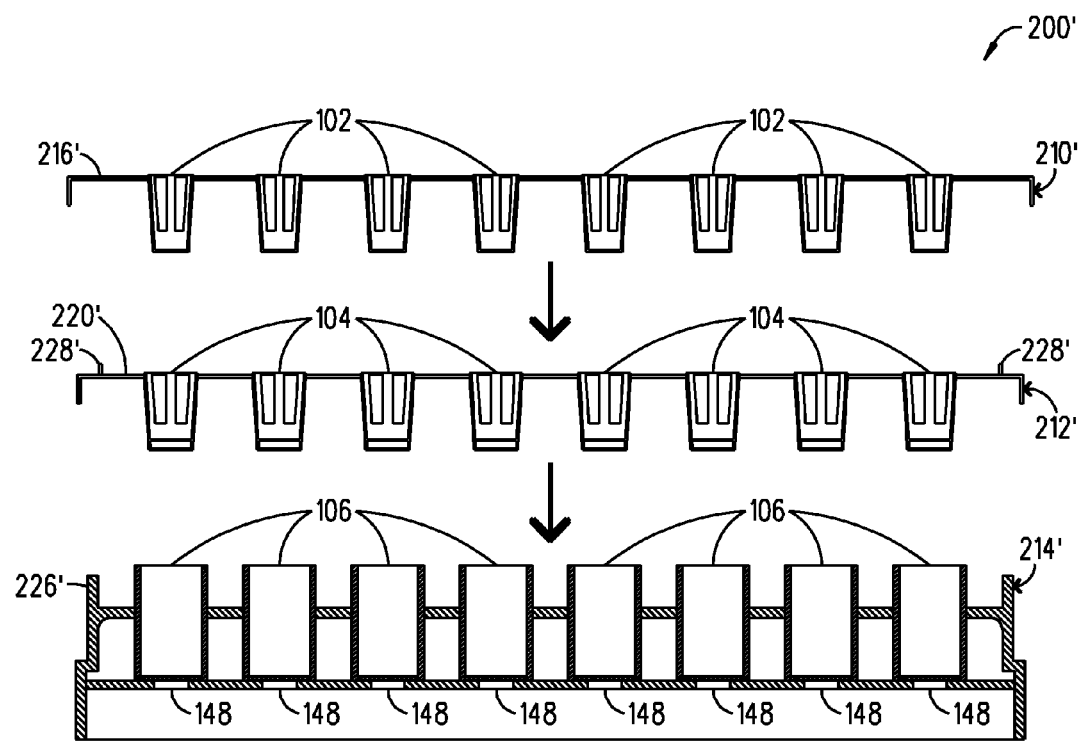
Figure 2E:
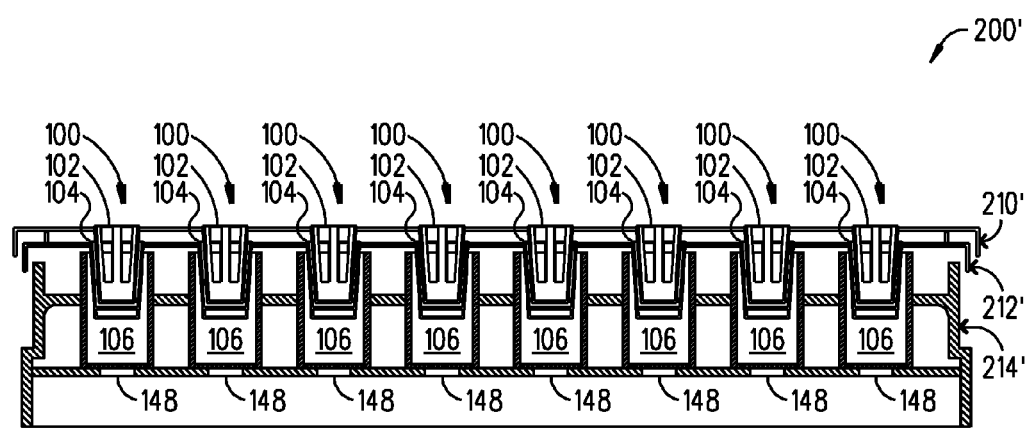

Referring to FIGS. 2C-2E, there are respectively illustrated a perspective view, and two cross-sectional side views of multiple nested permeable support devices 100 (ninety six shown) that are coupled to one another to form an exemplary microplate 200'. The microplate 200' includes a first insert plate 210', a second insert plate 212', and a reservoir plate 214'. The first insert plate 210' includes a frame 216' that supports an array of first inserts 102 (ninety six shown). The second insert plate 212' includes a frame 220' that supports an array of second inserts 104 (ninety six shown). The reservoir plate 214' includes a frame 226' that supports an array of reservoirs 106 (ninety six shown) the bottoms of which incorporate the optional biosensors 148. FIG. 2D shows a cross-sectional side view of the microplate 200' where the first insert plate 210' is separated from the second insert plate 212', and the second insert plate 212' is separated from the reservoir plate 214'. FIG. 2E shows a cross-sectional side view of the microplate 200' where the first insert plate 210' is placed on the second insert plate 212', and the second insert plate 212' is placed on the reservoir plate 214'. In this example, the second insert plate 212' has a support 228' extending upward from the frame 228' where the support 228' is sized to support the first insert plate 210' a desired distance from the second insert plate 212'. In this particular example, the second inserts 106 would not have the inner ledge 120 incorporated therein. The user can stack and separate the first insert plate 210', the second insert plate 212', and the reservoir plate 214' which is a desirable feature in that it enables the user to handle multiple nested permeable support devices 100 at the same time and also enables the user to have easy access to one or more of the first inserts 102, the second inserts 104 and the reservoirs 106.

The microplate 200' shown includes an array of ninety-six nested permeable support devices 100 but could have any number of permeable support devices 100. If desired, the microplate 200' could be configured to have SBS dimensions which would be well-suited to permit robotic handling.

In one application, the nested permeable support device 100 can be used to perform a first pass assay to determine the bioavailability of a NCE following absorption through the digestive tract and metabolism by the liver. For instance, a researcher can place a media in a growing reservoir and then place the first insert 102 in the growing reservoir. The first insert 102 is then filled with a volume of Caco 2 cells in media. The first insert 102 and growing reservoir are in communication until a confluent monolayer of Caco 2 cells is formed across the first permeable support 112. It usually takes about a month for Caco 2 cells to form across the first permeable support 112. The Caco 2 cells can be tested electronically to determine how tightly the Caco 2 cells adhere to one another by performing a TEER test, where a probe is inserted into the first well 108 and then the probe initiates a pulse that is detected by another probe located in the growing reservoir below the first permeable support 112. Another test that can be performed uses a dye called Lucifer yellow, which can pass through gaps in the Caco 2 cell monolayer. The more Lucifer yellow that shows up in the growing reservoir after being introduced in the first insert 102, the less mature (or confluent) the monolayer of Caco 2 cells. Tests such as these can be performed to make sure the Caco 2 cell culture is functioning as expected.

In parallel, the researcher can place a media in another growing reservoir and then place the second insert 104 in this growing reservoir. The second insert 104 is then filled with a volume of hepatocytes in media. The second insert 104 and reservoir are in communication until a confluent monolayer of hepatocytes is formed across the second permeable support 118. In this case, the second permeable support 118 could be coated with electrospun nanofibers such as the "Ultraweb™ Polyamine material which promotes a differentiated function of cultured hepatocytes. Tests could also be conducted to assure that the hepatocytes are functioning appropriately. Alternatively, the first insert 102 and second insert 104 can be placed in the reservoir 106 to grow the Caco 2 cells and the hepatocytes.

Once the Caco 2 cells and the hepatocytes have been cultured, the first and second inserts 102 and 104 would be lifted out of their respective growing reservoirs. The second insert 104 would be placed (nested) in the reservoir 106 which contains a media. Some media would then be placed above the layer of hepatocytes located within the second insert 104. Then, the first insert 102 would be placed (nested) in the second insert 104. The NCE and media would be dispensed above the layer of Caco 2 cells located within the first insert 102. After a period of incubation, the first insert 102 could be removed and the media in the second insert 104 could be tested (i.e., LS/MS) to determine if the NCE passed through the intestinal epithelium (Caco 2 cells). If the NCE did pass through the Caco 2 cells, then the second insert 104 could be removed and the media in the reservoir 106 could be tested (i.e., LC/MS) to check the bioavailability of the NCE and/or how the NCE is metabolized by the liver (hepatocytes) to form metabolic products. The hepatocytes could also show if the NCE is toxic at the dosage applied. If there are target cells (or molecules) on the bottom 128 of the reservoir 106, then these could be examined (i.e., LC/MS) to determine the drug effects either microscopically, or by using an assay that is separate from the Caco 2 cells and hepatocytes by pulling out the inserts 102 and 104. Alternatively, the target cells (or molecules) on the bottom 128 of the reservoir 106 could be examined by using an interrogation system to interrogate the biosensor 148 which is located in the bottom 128 of the reservoir 106 (cf. the aforementioned U.S. Patent Publication No. 2007 0020689 A1 and U.S. Patent Publication No. 2004 0091397 A1). This process is marked improvement over the state-of-the art since rather than requiring separate experiments to be conducted and data correlated to obtain information related to the "first pass effect" of the NCE, the nested permeable support device 100 permits this assessment to occur in one experiment.

In other applications, the nested permeable support device 100 can be used to test a NCE which would not pass through the digestive tract but instead would enter the body via inhalation in which case the Caco 2 cells would be replaced with nasal mucosal cells, bronchial cells or lung epithelial cells etc. In practice, the researcher would typically select the actual cells used in the nested permeable support device 100.

Figure 3A:
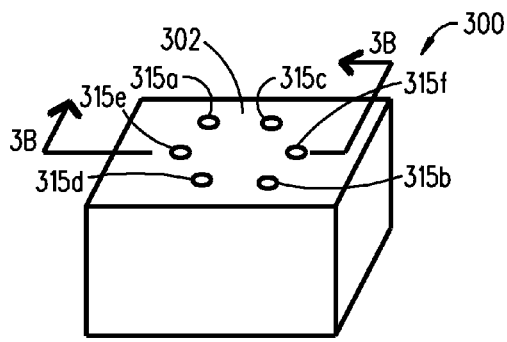
FIGS. 3A-3I show different views of an exemplary nested permeable support device configured in accordance with another embodiment of the present invention.
Figure 3B:
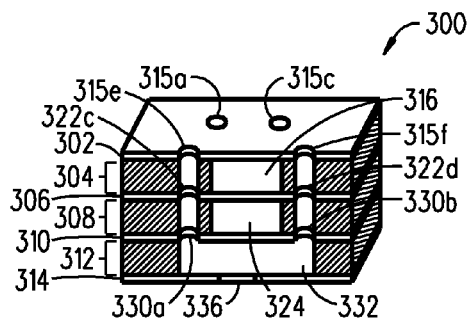

Referring to FIGS. 3A-3I, there are shown several different diagrams of an exemplary nested permeable support device 300 in accordance with another embodiment of the present invention. In FIGS. 3A-3B, there are respectively illustrated a perspective view and a cross-sectional perspective view of the nested permeable support device 300. The nested permeable support device 300 includes a first gas permeable film 302, a first sheet 304, a first permeable support 306, a second sheet 308, a second permeable support 310, a third sheet 312, and a receiver plate 314 (second gas permeable film 314). These materials 302, 304, 306, 308, 310, 312 and 314 may all be die cut and stacked-on one another to form what can be referred to as a three-chamber laminated nested permeable support device 300.

Figure 3C:
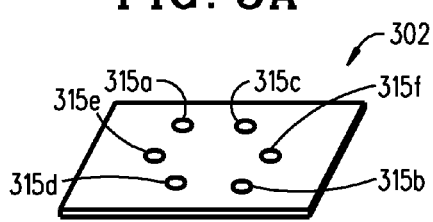
Figure 3D:
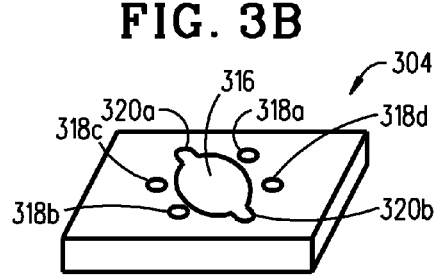
Figure 3E:
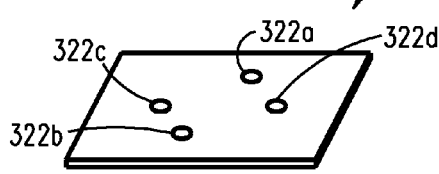
Figure 3F:
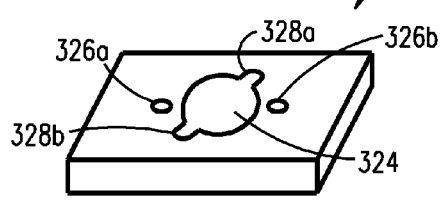
Figure 3G:
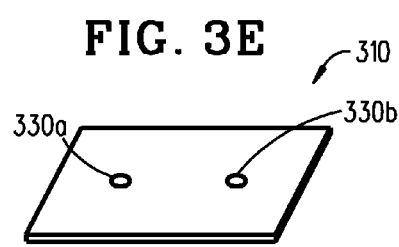
Figure 3H:
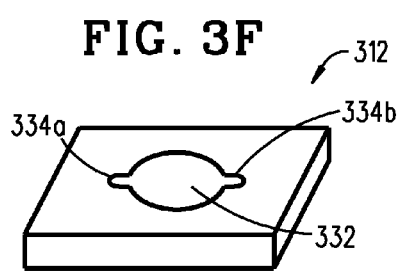
Figure 3I:
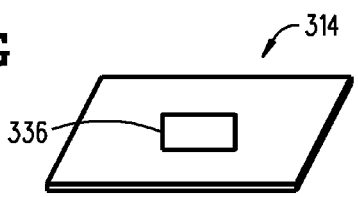

The first gas permeable film 302 (e.g., polyolefin, polystyrene) in this example has six openings 315a, 315b, 315c, 315d, 315e and 315f the purpose of which will become apparent in the discussion below (see FIG. 3C). The first gas permeable film 302 is attached to a top of the first sheet 304 (e.g., polyolefin, polystyrene). The first sheet 304 has one opening therein that forms a first well 316 (first chamber 316). In addition, the first sheet 304 has four openings 318a, 318b, 318c and 318d the purpose of which will become apparent in the discussion below (see FIG. 3D). The first gas permeable film 302 provides access to the first well 316 by using two openings 315a and 315b formed therein which are respectively in communication with two sections 320a and 320b of the first well 316. The first sheet 304 has a bottom on which there is attached the first permeable support 306 (e.g., a track-etched membrane 306, a woven material 306, a non-woven material 306, a cast material 306). The first permeable support 306 not only forms the bottom of the first well 316 but also has four openings 322a, 322b, 322c and 322d the purpose of which will become apparent in the discussion below (see FIG. 3E).

The first permeable support 306 is attached to a top of the second sheet 308 (e.g., polyolefin, polystyrene). The second sheet 308 has one opening therein that forms a second well 324 (second chamber 324). In addition, the second sheet 308 has two additional openings 326a and 326b the purpose of which will become apparent in the discussion below (see FIG. 3F). The first gas permeable film 302, the first sheet 304, and the first permeable support 306 provides access to the second well 324 by respectively using openings 315c, 315d, 318a, 318b, 322a and 322b formed therein which are in communication with two sections 328a and 328b of the second well 324. The second sheet 308 has a bottom on which there is positioned the second permeable support 310 (e.g., e.g., a track-etched membrane 310, a woven material 310, a non-woven material 310, a cast material 310). The second permeable support 310 not only forms the bottom of the second well 324 but also has two openings 330a and 330b the purpose of which will become apparent in the discussion below (see FIG. 3G).

The second permeable support 310 is attached to a top of the third sheet 312 (e.g., polyolefin, polystyrene). The third sheet 312 has one opening therein that forms a third well 332 (second chamber 332) which in this example is larger than the first and second wells 316 and 324 (see FIG. 3H). The first gas permeable film 302, the first sheet 304, the first permeable support 306, the second sheet 308, and the second permeable support 310 provides access to the third well 332 by respectively using openings 315e, 315f, 318c, 318d, 322c, 322d, 326a, 326b, 330a and 330b formed therein which are in communication with two sections 334a and 334b of the third well 332. The third sheet 312 has a bottom on which there is positioned the receiver plate 314 (second gas permeable film 314) (see FIG. 3I). The receiver plate 314 could be made with an optically clear, possibly gas-permeable material to facilitate high-content screening. Another option for the receiver plate 314 would be to have it feature a biosensor 336 (e.g., grating-based planar waveguide sensor, grating-based surface plasmon resonance sensor, prism-based surface plasmon resonance sensor). Alternatively, the nested permeable support device 300 could be configured to have one opening or more than two openings which have access to each well 316, 324 and 332 rather than the aforementioned two openings which have access to each well 316, 324 and 332. At least two openings to each well 316, 324 and 332 would be desirable to help avoid air entrapment within the wells 316, 324 and 332. In addition, the nested permeable support device 300 could have any number of nested wells formed therein rather than the aforementioned three wells 316, 324 and 332.

Figure 4A:
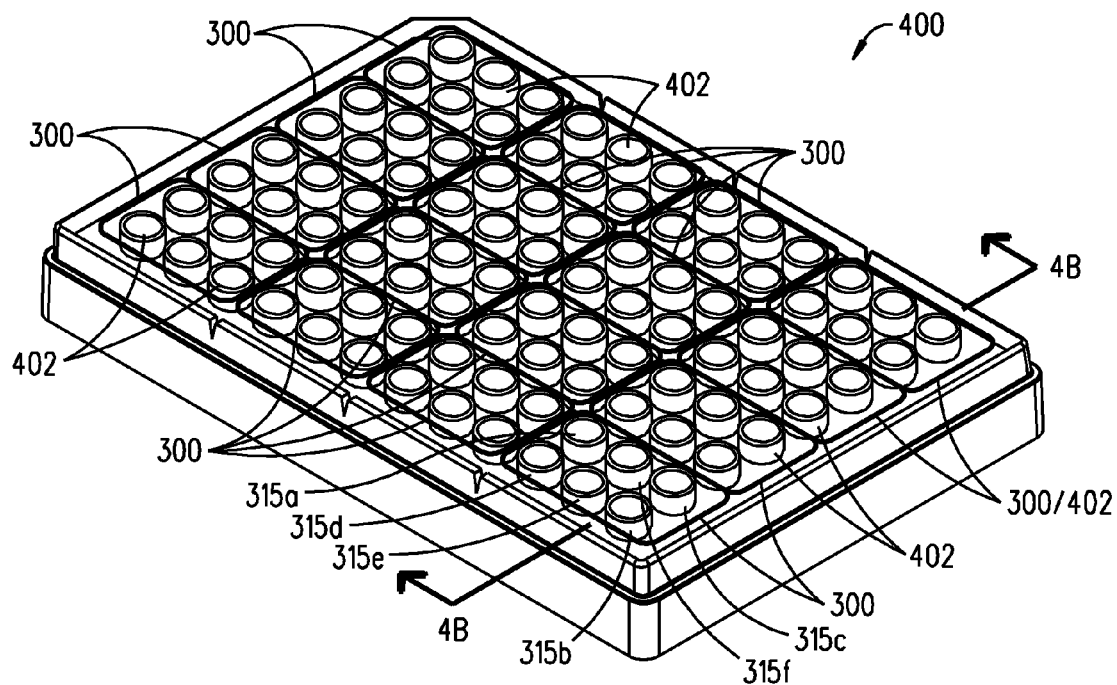
FIGS. 4A-4B respectively illustrate a perspective view and a cross-sectional side view of several nested permeable support devices shown in FIGS. 3A-3I that are configured to form an exemplary microplate.
Figure 4B:
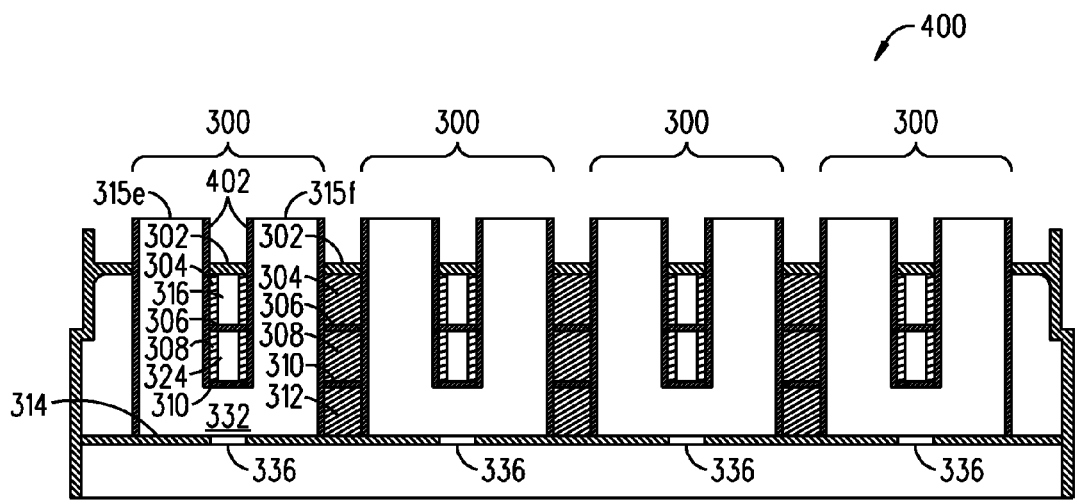

A person could use a single nested permeable support device 300 to perform an experiment to test a NCE. Alternatively, the person could use multiple nested permeable support devices 300 in a multiwell format to perform multiple experiments at the same time. Referring to FIGS. 4A-4B, there are respectively illustrated a perspective view and a cross-sectional side view of an exemplary microplate 400 incorporating sixteen nested permeable support devices 300. This exemplary microplate 400 has a 96-well plate format where each set of six wells 402 would correspond with one of the nested permeable supports 300. As shown, each set of six wells 402 could also correspond with the six openings 315a, 315b, 315c, 315d, 315e and 315f in the first gas permeable film 302 of the nested permeable support 300. Alternatively, a microplate with a 384-well plate format could be used which in this case it could incorporate 64 nested permeable support devices 300. Also, a microplate with a 1536-well plate format could be used which in this case it could incorporate 256 nested permeable support devices 300. Basically, a microplate with X-well plate format could be used to incorporate any number of nested permeable support devices 300 and if the microplate had SBS dimensions then it would be well-suited to permit robotic handling.

In one application, the nested permeable support device 300 can be used to perform a first pass assay to determine the bioavailability of a NCE following absorption through the digestive tract and metabolism by the liver. For instance, a researcher can fill the first well 316 with the proper cell type such as Caco 2 cells suspended in a media. The Caco 2 cells would settle onto the first permeable support 306 where they will attach and grow until they are ready for the assay. If the growth time required is long enough to require multiple feedings then the fluid in the first well 316 would be aspirated and replaced with fresh media. In parallel, the researcher can fill the second well 324 with the proper cell type such as hepatocytes suspended in a media. The hepatocytes would settle onto the second permeable support 310 where they will attach and grow until they are ready for the assay. If the growth time required is long enough to require multiple feedings then the fluid in the second well 324 would be aspirated and replaced with fresh media. During this time, the third well 332 could be filled with media and if desired target cells (or molecules) which would attach to the receiver plate 314.

Once the Caco 2 cells and the hepatocytes have been cultured, the NCE and media would be dispensed in the first well 316 above the layer of Caco 2 cells. After a period of incubation, the media in the third well 332 would be interrogated by an assay of interest. For example, the media in the third well 332 could be interrogated (i.e., LC/MS) to determine if the NCE passed through the intestinal epithelium (Caco 2 cells) and the liver (hepatocytes). If there are target cells on the receiver plate 314 of the third well 332, then these could be examined (i.e., LC/MS) to determine the effect caused by the NCE. Alternatively, the target cells (or molecules) on the bottom of the reservoir 106 could be examined by using an interrogation system to interrogate the biosensor 336 which is located in the receiver plate 314 (cf the aforementioned U.S. Patent Publication No. 2007 0020689 A1 and U.S. Patent Publication No. 2004 0091397 A1). This process is a marked improvement over the state-of-the art since rather than requiring separate experiments to be conducted and data correlated to obtain information related to the "first pass effect" of the NCE, the nested permeable support device 300 permits this assessment to occur in one experiment.

In other applications, the nested permeable support device 300 can be used to test a NCE which would not pass through the digestive tract but instead would enter the body via inhalation in which case the Caco 2 cells would be replaced with nasal mucosal cells, bronchial cells or lung epithelial cells etc. In practice, the researcher would typically select the actual cells used in the nested permeable support device 300.

In view of the foregoing discussion, it should be appreciated that the nested permeable support device 100 and 300 would provide an in vivo-like situation for pharmaceutical companies to perform "first pass assays" and other assays to test different NCEs. The nested permeable support device 100 and 300 utilizes at least two permeable supports 112, 118, 306 and 310 to develop two polarized cell populations individually, and then provides a structure for layering the permeable supports 112, 118, 306 and 310 to conduct these assays. Either permeable support 112, 118, 306 and 310 may be treated or coated to enhance the culture of specific cell types such as Caco 2 cells and hapatocytes. The permeable supports 112, 118, 306 and 310 could be a track-etched membrane, a woven, non-woven, or cast material, and possibly decorated with cell binding sequences or ASGPR agonists. If desired, the permeable support 118 and 310 for the culture of hepatocytes could be enhanced by the addition of electrospun nanofibers formed, for instance, as disclosed in co-assigned PCT patent application WO2007/144355 A1 (the contents of which are incorporated by reference herein) or coated with hepatocyte activity promoting materials such as locust bean gum, collagen or other ECM materials. Thus, the nested permeable support device 100 and 300 make it possible to determine ADME-Tox, pharmacokinetic properties and target selectivity in a reduced number of assays when compared to state-of-the-art devices. This in turn decreases the time, labor and materials required for drug discovery. Additionally, more relevant data would be provided through the cell growth on the permeable supports 112, 118, 306 and 310 that could enhance the maintenance of more in vivo-like cell functions, and promote intercellular communication.

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

The invention claimed is:

1. A nested permeable support device, comprising:
a first sheet having an opening used to form a first well, where the first sheet has a top on which there is attached a gas permeable film and a bottom on which there is attached a first permeable support, where the gas permeable film has at least one opening formed therein to provide access only to the first well, and where the first permeable support is configured to allow a chemical entity to pass through but restrict movement there through of cells;
a second sheet having an opening used to form a second well, where the second sheet has a top on which there is attached the first permeable support and a bottom on which there is attached a second permeable support, where each of the gas permeable film, the first sheet and the first permeable support has at least one opening formed therein to provide access only to the second well; and where the second permeable support is configured to allow the chemical entity to pass through but restrict movement there through of cells; and
a third sheet having an opening used to form a third well, where the third sheet has a top on which there is attached the second permeable support and a bottom on which there is attached a receiver plate, and where each of the gas permeable film, the first sheet, the first permeable support, the second sheet and the second permeable support has at least one opening formed therein to provide access only to the third well.

2. The nested permeable support device of claim 1, wherein the first well, the second well and the third well are part of a multiwell plate.

3. The nested permeable support device of claim 1, wherein the first permeable support includes one of:
a track-etched membrane;
a woven material;
a non-woven material; and
a cast material.

4. The nested permeable support device of claim 1, wherein the second permeable support includes one of:
a track-etched membrane;
a woven material;
a non-woven material; and
a cast material.

5. The nested permeable support device of claim 1, wherein:
the first permeable support has formed thereon Caco 2 cells, nasal mucosal cells, bronchial cells or lung epithelial cells; and
the second permeable support has formed thereon hepatocytes.

6. The nested permeable support device of claim 1, further comprising a biosensor incorporated within the bottom of the third well.

7. A nested permeable support device, comprising:
a first sheet having an opening used to form a first well, where the first sheet has a top on which there is attached a gas permeable film and a bottom on which there is attached a first membrane support, where the gas permeable film has at least one opening formed therein to provide access only to the first well;
a second sheet having an opening used to form a second well, where the second sheet has a top on which there is attached the first membrane support and a bottom on which there is attached a second membrane support, where each of the gas permeable film, the first sheet and the first membrane support has at least one opening formed therein to provide access only to the second well; and
a third sheet having an opening used to form a third well, where the third sheet has a top on which there is attached the second membrane support and a bottom on which there is attached a receiver plate, and where each of the gas permeable film, the first sheet, the first membrane support, the second sheet and the second membrane support has at least one opening formed therein to provide access only to the third well.

8. The nested permeable support device of claim 7, wherein:
the first membrane support has formed thereon Caco 2 cells, nasal mucosal cells, bronchial cells or lung epithelial cells; and
the second membrane support has formed thereon hepatocytes.

9. The nested permeable support device of claim 7, wherein the first membrane support and the second membrane support permit passage there through of a chemical entity.

10. The nested permeable support device of claim 7, further comprising a biosensor incorporated within the bottom of the third well.

11. The nested permeable support device of claim 7, wherein the first well, the second well and the third well are part of a multiwell plate.

* * * * *